(12) United States Patent
Kateraas et al.

(10) Patent No.: US 8,936,552 B2
(45) Date of Patent: Jan. 20, 2015

(54) PHYSICAL ACTIVITY MONITOR AND DATA COLLECTION UNIT

(75) Inventors: Espen D. Kateraas, Aliso Viejo, CA (US); Pedro J. Medelius, Merritt Island, FL (US)

(73) Assignee: HeartMiles, LLC, Aliso Viejo, CA (US)

( * ) Notice: Subject to any disclaimer, the term of this patent is extended or adjusted under 35 U.S.C. 154(b) by 536 days.

(21) Appl. No.: 12/992,206

(22) PCT Filed: May 13, 2009

(86) PCT No.: PCT/US2009/043753
§ 371 (c)(1),
(2), (4) Date: Feb. 15, 2011

(87) PCT Pub. No.: WO2009/140360
PCT Pub. Date: Nov. 19, 2009

(65) Prior Publication Data
US 2011/0152637 A1      Jun. 23, 2011

Related U.S. Application Data

(60) Provisional application No. 61/071,701, filed on May 14, 2008.

(51) Int. Cl.
*A61B 5/00* (2006.01)
*A61B 5/0205* (2006.01)
(Continued)

(52) U.S. Cl.
CPC ..... *A61B 5/02055* (2013.01); *A61B 2562/0219* (2013.01); *A61B 5/1455* (2013.01); *A61B 5/681* (2013.01); *A61B 5/1118* (2013.01); *A61B 5/02438* (2013.01)
USPC ......................................................... 600/301

(58) Field of Classification Search
CPC .... A61B 5/02438; A61B 5/02; A61B 5/6824; A61B 5/72; A61B 5/1455; A61B 5/681; A61B 5/1118; A61B 5/0219; A61B 5/02055; A63B 24/0062
See application file for complete search history.

(56) References Cited

U.S. PATENT DOCUMENTS 4,566,461 A * 1/1986 Lubell et al. ................... 600/481
5,575,284 A * 11/1996 Athan et al. ................... 600/323
(Continued)

FOREIGN PATENT DOCUMENTS

EP          1 702 560 A       9/2006
JP          2004-136105       5/2004
(Continued)

OTHER PUBLICATIONS

Faculty of Mathematics, Computer Science, Physics, and Astronomy, "Organization and Design of Autonomous Systems", University of Amsterdam, Aug. 1999.*

(Continued)

*Primary Examiner* — William Thomson
*Assistant Examiner* — Scott T. Luan
(74) *Attorney, Agent, or Firm* — Finnegan, Henderson, Farabow, Garrett & Dunner, LLP

(57) ABSTRACT

A physical activity data collection unit includes one or more infrared sensors configured to provide an output indicative of a pulse rate of a user of the physical activity data collection unit, at least one temperature sensor configured to provide an output indicative of at least a body temperature of the user, and at least one accelerometer configured to provide an output indicative of movements of the user. The physical activity data collection unit can also include a microcontroller configured to determine a pulse rate, a body temperature, and movement characteristics of the user of the data collection unit based on outputs from the one or more infrared sensors, the at least one temperature sensor, and the at least one accelerometer; determine a physical exertion level of the user based on one or more of the pulse rate, the body temperature, or the movement characteristics of the user; and store, in a memory, data indicative of the physical exertion level during a time period during which the physical exertion level exceeds a predetermined threshold.

25 Claims, 2 Drawing Sheets

(51) Int. Cl.
*A61B 5/11* (2006.01)
*A61B 5/024* (2006.01)
*A61B 5/1455* (2006.01)

(56) References Cited

U.S. PATENT DOCUMENTS

| | | | |
|---|---|---|---|
| 5,626,140 A * | 5/1997 | Feldman et al. | 600/484 |
| 5,941,837 A | 8/1999 | Amano | |
| 6,039,688 A | 3/2000 | Douglas et al. | |
| 6,151,586 A | 11/2000 | Brown | |
| 6,167,362 A | 12/2000 | Brown et al. | |
| 6,240,393 B1 | 5/2001 | Brown | |
| 6,585,622 B1 | 7/2003 | Shum et al. | |
| 6,687,535 B2 * | 2/2004 | Hautala et al. | 600/520 |
| 7,328,053 B1 * | 2/2008 | Diab et al. | 600/336 |
| 7,901,326 B2 * | 3/2011 | Niva et al. | 482/9 |
| 7,993,276 B2 | 8/2011 | Nazarian et al. | |
| 8,292,820 B2 * | 10/2012 | Punkka et al. | 600/484 |
| 8,512,238 B2 * | 8/2013 | Nissila et al. | 600/300 |
| 2002/0013717 A1 | 1/2002 | Ando et al. | |
| 2004/0010420 A1 | 1/2004 | Rooks | |
| 2004/0236233 A1 | 11/2004 | Kosuda et al. | |
| 2005/0015281 A1 | 1/2005 | Clark et al. | |
| 2005/0071197 A1 | 3/2005 | Goldberg | |
| 2005/0102172 A1 | 5/2005 | Sirmans, Jr. | |
| 2005/0182302 A1 | 8/2005 | Johnson et al. | |
| 2006/0025282 A1 | 2/2006 | Redmann | |
| 2006/0094938 A1 | 5/2006 | Shimada et al. | |
| 2006/0111944 A1 | 5/2006 | Sirmans, Jr. et al. | |
| 2006/0241973 A1 | 10/2006 | Harris | |
| 2006/0287883 A1 | 12/2006 | Turgiss et al. | |
| 2007/0033069 A1 | 2/2007 | Rao et al. | |
| 2007/0123786 A1 * | 5/2007 | Grandjean et al. | 600/509 |
| 2007/0136093 A1 | 6/2007 | Rankin et al. | |
| 2007/0255126 A1 * | 11/2007 | Moberg et al. | 600/365 |
| 2007/0260482 A1 | 11/2007 | Nurmela et al. | |
| 2007/0260511 A1 | 11/2007 | Bender, II | |
| 2008/0088436 A1 * | 4/2008 | Reeves et al. | 340/539.12 |
| 2008/0147502 A1 | 6/2008 | Baker | |
| 2008/0162186 A1 | 7/2008 | Jones | |
| 2009/0048540 A1 * | 2/2009 | Otto et al. | 600/595 |
| 2009/0096573 A1 * | 4/2009 | Graessley | 340/5.8 |
| 2009/0177097 A1 * | 7/2009 | Ma et al. | 600/500 |

FOREIGN PATENT DOCUMENTS

| | | |
|---|---|---|
| JP | 2006-119986 | 5/2006 |
| JP | 2006-129887 | 5/2006 |
| JP | 2006-136422 | 6/2006 |
| JP | 2007-213196 | 8/2007 |
| JP | 2007 213196 A | 8/2007 |
| WO | WO 2006/036911 | 4/2006 |
| WO | WO 2006/044677 | 4/2006 |
| WO | WO 2006/044677 A | 4/2006 |
| WO | WO 2007/100959 A2 | 9/2007 |

OTHER PUBLICATIONS

International Search Report; International Patent Application No. PCTIUS2009/043753; Filed May 13, 2009; Applicant: EspenUSA Holding, LLC, mailed Aug. 27, 2009, 3 pages.

First Official Action dated Feb. 14, 2012 from the Chinese Patent Office in corresponding Chinese Patent Application No. 200980127540.3, 7 pages.

Notice of Reasons for Rejection in corresponding Japanese Application No. 2011-509641, mailed on Jul. 30, 2013, 3 pages.

* cited by examiner

PHYSICAL ACTIVITY MONITOR AND DATA COLLECTION UNIT

This application claims priority to U.S. Provisional Patent Application No. 61/071,701, filed on May 14, 2008, the contents of which are fully incorporated herein by reference.

TECHNICAL FIELD

The present disclosure relates to a sensor-based device configured to monitor the physical activity level of an individual, collect data during periods of physical exertion, and transmit the collected data to a data collection portal associated with a physical activity rewards allocation system and/or a physical activity tracking system.

SUMMARY OF THE INVENTION

One aspect of the disclosure includes a physical activity data collection unit that includes one or more infrared sensors configured to provide an output indicative of a pulse rate of a user of the physical activity data collection unit, at least one temperature sensor configured to provide an output indicative of at least a body temperature of the user, and at least one accelerometer configured to provide an output indicative of movements of the user. The physical activity data collection unit can also include a microcontroller configured to determine a pulse rate, a body temperature, and movement characteristics of the user of the data collection unit based on outputs from the one or more infrared sensors, the at least one temperature sensor, and the at least one accelerometer; determine a physical exertion level of the user based on one or more of the pulse rate, the body temperature, or the movement characteristics of the user; and store, in a memory, data indicative of the physical exertion level during a time period during which the physical exertion level exceeds a predetermined threshold.

Another aspect of the disclosure includes a physical activity data collection unit including at least one physiological sensor configured to generate an output related to the physical activity level of a user and a microcontroller configured to: monitor the output of the at least one physiological sensor; determine a physical exertion level of the user based on the output of the at least one physiological sensor; and store, in a memory, data indicative of the physical exertion level during a time period during which the physical exertion level exceeds a predetermined threshold.

Yet another aspect of the disclosure includes a physical activity data collection unit that includes one or more infrared sensors configured to provide an output indicative of a pulse rate of a user of the physical activity data collection unit; at least one temperature sensor configured to provide an output indicative of at least a body temperature of the user; at least one accelerometer configured to provide an output indicative of movements of the user; and a microcontroller. The microcontroller may be configured to: sample the outputs of the one or more infrared sensors, the at least one temperature sensor, and the at least one accelerometer; and store, in a memory, data derived from the sampled outputs of the one or more infrared sensors, the at least one temperature sensor, and the at least one accelerometer.

DETAILED DESCRIPTION

Figure 1:
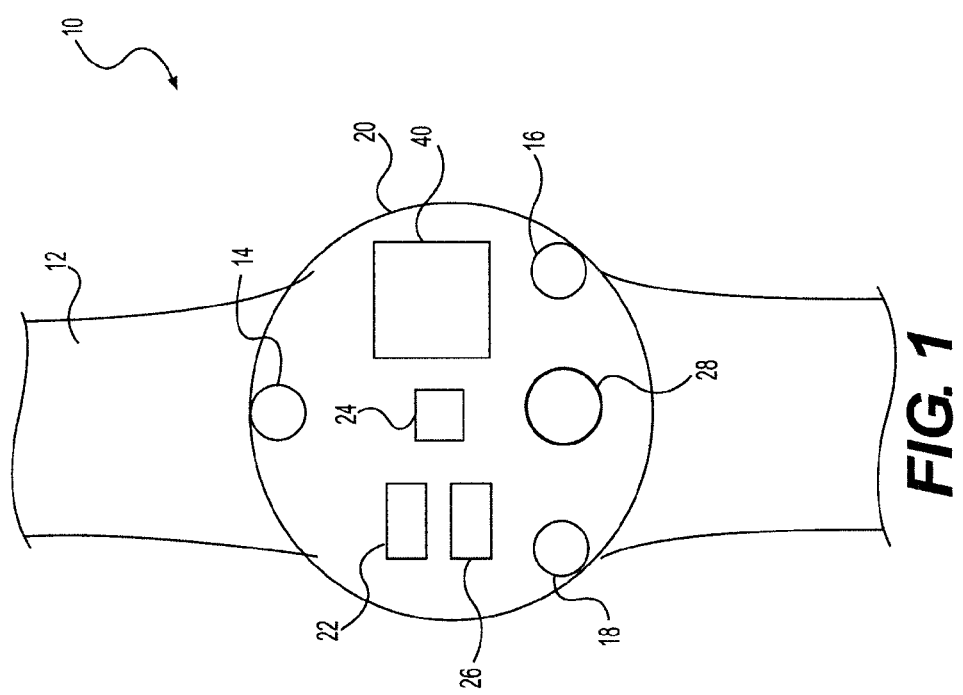
FIG. 1 is a diagrammatic representation of a data collection unit according to an exemplary disclosed embodiment.

FIG. 1 provides diagrammatic representation of a data collection unit according to an exemplary disclosed embodiment. As illustrated in FIG. 1, the disclosed data collection unit 10 may be configured as a wearable article. In certain embodiments, for example, the data collection unit may be incorporated into an article wearable on an individual's wrist. Such an article would offer the advantage of being minimally intrusive, as most people are accustomed to wearing articles fastened to the wrist. The wrist unit could be fashioned as a simple wrist band stylized in various colors and patterns. The band may be adjustable, shockproof, and secured to the wrist using a hook and loop closure, a buckle closure, an elastic material requiring no separate closure device, or with any other suitable fastening configuration. The band can be made from various materials including, for example, a waterproof material, neoprene, polymer, nylon, leather, metal, or any other wearable material.

In one embodiment, data collection unit 10 may be embedded into a small, self-contained wrist band 12. In such a configuration, there may be little or no external indication of the presence of the hardware components of the data collection unit. In other embodiments, the data collection unit may be incorporated into a watch, bracelet, heart rate monitor or other wearable article to provide added functionality to those devices. In addition to the wrist, the disclosed data collection unit may be positioned over any portion of a user's body (e.g., the neck, chest, ankle, head, or thigh) that can provide suitable access to the biological markers needed for monitoring the user's level of physical exertion. For example, the data collection unit may be configured as or incorporated into shoe soles, ear clips, a necklace, ankle band, sock, belt, glove, ring, sunglasses, hat, and/or a headband.

Data collection unit 10 includes a sensor array (including one or more sensors) configured to monitor biological markers that vary with the level of exertion of an individual. The monitored biological markers may include, for example, pulse rate, body temperature, blood oxygen content, or any other suitable marker. Within the sensor array, each sensor may be configured to monitor only a single biological marker. Alternatively, an individual sensor in the array may be configured to monitor multiple biological markers.

In one embodiment, data collection unit 10 may include several sensors. These sensors may include any arrangement of one or more sensors capable of monitoring biological characteristics and/or movement associated with a user of data collection unit 10. In one exemplary embodiment, as shown in FIG. 1, data collection unit 10 may include at least one infrared sensor 14, a temperature sensor 22, and/or an accelerometer 24.

In the exemplary embodiment shown in FIG. 1, data collection unit 10 includes three infrared sensors 14, 16, 18. Suppliers of appropriate infrared transmitter/receivers include Vishay Semiconductors, among others.

Each infrared sensor may be configured as a transmitter/receiver capable of monitoring the oxygen content of blood passing through nearby blood vessels. Specifically, each infrared sensor can be configured to both emit infrared radiation into the body of the wearer of data collection unit 10 and detect the level of infrared radiation received at the sensor. The wavelength of the emitted radiation can be selected according to the requirements of a particular application. In one embodiment, infrared sensors 14, 16, and 18 can be configured to emit infrared radiation in a wavelength range of about 650 nm to about 950 nm.

The difference between the emitted radiation level and the detected radiation level is characteristic of the amount of infrared radiation absorbed by the body and, especially, by oxygen-carrying blood. This sensed absorption level can be used to determine the pulse rate of the wearer of data collection unit 10. Particularly, the infrared absorption level may be affected by the expansion and contraction of nearby blood vessels and the oxygen content of blood passing through nearby vessels, which are both physical characteristics that vary together with heart rate. Thus, the rate of observed changes in infrared absorption characteristics of the body can enable a calculation of the wearer's heart rate.

While only one infrared sensor may be needed depending on the functional requirements of a particular embodiment, including two or more infrared sensors, or even three or more infrared sensors, can serve to increase the reliability of the data collected from these sensors. As illustrated in FIG. 1, infrared sensors 14, 16, and 18 may be spaced apart from one another. In certain embodiments, these sensors may be located along a perimeter of a central housing 20 of data collection unit 10. Spacing infrared sensors 14, 16, and 18 apart from one another can maximize the possibility that at least one sensor contacts the wearer's skin at all times, even during the movements associated with physical activities.

A power management scheme may be employed to lower the power requirements of infrared sensors 14, 16, and 18. For example, the transmitter portion of each sensor may be pulsed at a predetermined duty cycle to conform to the power specifications of a particular configuration. In one exemplary embodiment, the infrared transmitters of sensors 14, 16, and 18 can be pulsed using a 1% duty cycle at a rate of about 8 pulses per second.

Data collection unit 10 may also include a temperature sensor 22. Temperature sensor 22 may be configured to monitor the body temperature of the wearer of data collection unit 10 by measuring the temperature outside of housing 20 and, for example, against the skin of the wearer. Additionally, temperature sensor 22 may be configured to measure the temperature inside housing 20. Using the difference between the temperature measurements from inside and outside of housing 20, it can be determined whether an observed temperature change outside of the housing is likely attributable to atmospheric conditions or an actual change in body temperature of the wearer of data collection unit 10. While certain embodiments may include only one temperature sensor, other embodiments may include multiple temperature sensors in order to meet a desired set of operational characteristics (e.g., monitoring body temperature from multiple locations on data collection unit 10; separate temperature sensors to monitor the temperature inside and outside of housing 20; etc.).

Temperature sensor 22 may include any suitable device for ascertaining the body temperature of an individual. For example, temperature sensor 22 may include a digital or analog device and may include thermocouples, diodes, resistance temperature detectors (RTDs), or infrared detectors. Suitable temperature sensors may be obtained from various suppliers, including Analog Devices Inc., Omega, or Texas Instruments. For certain types of temperature sensors, contact with the individual's skin may aid in obtaining accurate body temperature measurements. On the other hand, in certain instances where, for example, infrared sensors provide the primary mode of measuring body temperature, mere proximity to the individual's skin may be sufficient to accurately determine body temperature of the user.

Additionally, data collection unit 10 may include an accelerometer 24 to monitor motion of data collection unit 10. In certain embodiments, accelerometer 24 includes only a single axis accelerometer configured to detect motion along one axis. Other embodiments, however, may include multiple accelerometers. In one exemplary embodiment, accelerometer 24 may include a three-axis accelerometer, which includes three accelerometers arranged orthogonally with respect to one another. With such an arrangement, accelerometer 24 may be able to detect or monitor movements along three separate axes.

A three-axis accelerometer may be especially useful for the detection of movements associated with exercise and certain types of physical activity. Generally, most sports or types of physical activity produce a signature pattern of movements that can be detected using an accelerometer. In this way, accelerometer 24 can help confirm whether the wearer of data collection unit 10 is engaged in physical activity and, in certain cases, can help determine the type of sport or activity in which the wearer is engaged.

Other embodiments of data collection unit 10 may include additional or different sensors. For example, data collection unit 10 may include a carbon dioxide detector, additional accelerometers, a breathing rate sensor, or any other type of sensor suitable for monitoring physical activity levels.

In addition to the infrared sensors described above, the pulse of the wearer of data collection unit 10 may be ascertained using any other type of sensor suitable for monitoring the wearer's heart rate. In one embodiment, for example, electro-cardiogram based technology may be incorporated into data collection unit 10.

Data collection unit 10 may also include a transceiver 26 for establishing communication with devices external to data collection unit 10. To address power requirements, data collection unit 10 may also include a battery 28.

Figure 2:
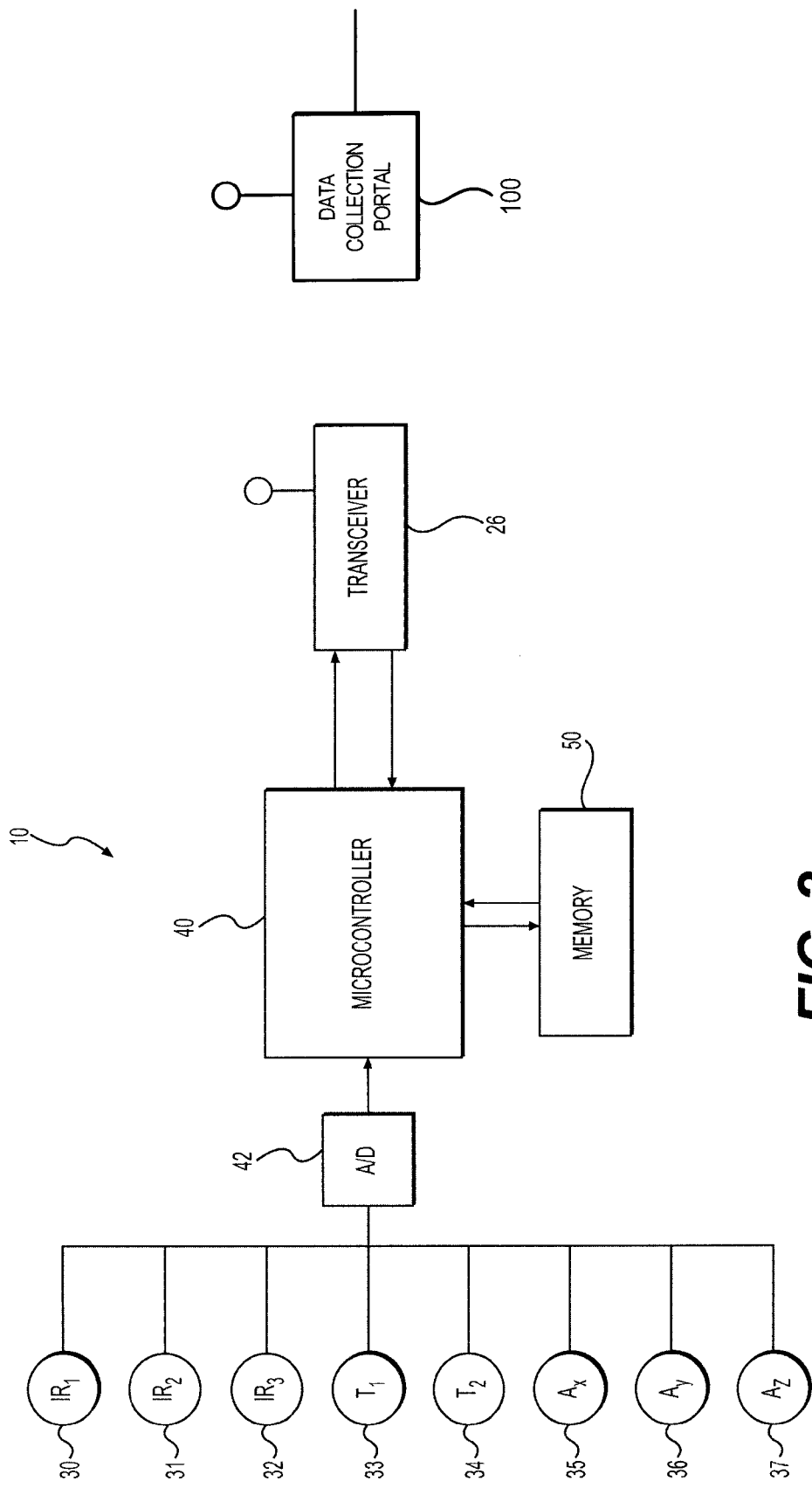
FIG. 2 is a functional block level diagram of a data collection unit according to an exemplary disclosed embodiment.

FIG. 2 provides a schematic, functional block level diagram of data collection unit 10, according to an exemplary disclosed embodiment. Within data collection unit 10, several sensed quantities can be provided to a microcontroller 40 for processing. For example, these sensed quantities may include outputs 30, 31, and 32 from infrared sensors 14, 16, and 18, respectively. Additionally, these sensed quantities may include temperature sensor outputs 33 and 34. Temperature output 33 may correspond to the temperature inside housing 20, for example, and temperature output 34 may correspond to the observed temperature outside of housing 20. The sensed quantities may also include accelerometer outputs 35, 36, and 37, each corresponding to a unique axis of movement.

Microcontroller 40 can store the data associated with the sensed quantities in a memory 50 in raw form or, alternatively, after processing. Further, the data relating to the sensed quantities can be transmitted to a remote location by transceiver unit 26.

Any suitable microcontroller 40 may be included in data collection unit 40. In one embodiment, microcontroller 40 includes a small microcontroller having dimensions of about 0.4 inches by 0.4 inches, or smaller. One suitable microcontroller includes the PIC18F series of microcontroller manufactured by Microchip Inc. Preferably, microcontroller 40 would exhibit low power characteristics and would require from about 10 microamps to about 50 microamps during normal operation and between 5 milliamps to about 20 milliamps while transmitting data.

Microcontroller 40 of data collection unit 10 has several responsibilities. Among these responsibilities, microcontroller 40 periodically collects data from the available sensors via an analog-to-digital converter 42. The frequency of data collection can be selected to meet the requirements of a particular application. In one embodiment, microcontroller 40 may sample the data from the sensors at least once per second. Higher or lower sampling frequencies, however, may also be possible.

Microcontroller 40 may be configured with the ability for selecting from among multiple data sampling frequencies depending on sensed conditions. For example, microcontroller 40 may be programmed to sample the sensor outputs slower than once per second (e.g., once per every 10 seconds) when microcontroller 40 determines that the user of the device is at rest or at a normal level of physical exertion. Similarly, microcontroller 40 may be configured to sample the sensor outputs more frequently (e.g., at least once per second) when the user's physical exertion level exceeds a predetermined threshold. In certain embodiments, and during periods of physical exertion, microcontroller 40 may collect sensor data up to five times per second, ten times per second, or even more, to ensure that rapidly changing quantities such as pulse rate and blood oxygen, which may cycle on the order of 200 times per minute during periods of extreme physical exertion, can be accurately evaluated.

When appropriate, microcontroller 40 may also enter a rest state to conserve power. For example, when infrared sensors 14, 16, or 18 provide no pulse readings or accelerometer 24 registers no movements over a certain period of time, microcontroller 40 may determine that data collection unit 10 is not being worn. Under such conditions, microcontroller 40 may slow the sensor sampling period to once every thirty seconds, once every minute, or to another suitable sampling frequency. Additionally, microcontroller 40 may be configured to sample only a portion of the available sensors during times of physical inactivity or when data collection unit 10 is not being worn. In one embodiment, for example, once microcontroller 40 determines that the user is not wearing data collection unit 10, microcontroller 40 may begin sampling the output of temperature sensor 22 alone. In such a configuration, a perceived rapid change in temperature may indicate that data collection unit 10 is in use and may prompt the controller to "wake up" and restore full functioning data collection.

Microcontroller 40 can be configured to analyze the data collected from the sensors onboard data collection unit 10. For example, data from infrared sensors 14, 16, 18 can be used to compare the transmitted infrared signal to the received infrared signal and calculate the blood oxygen saturation level via known algorithms. Microcontroller 40 may also be configured to calculate the pulse rate by monitoring the frequency of changes in the blood oxygen saturation level.

As noted above, microcontroller 40 can be configured to store raw or processed data in memory 50 included in data collection unit 10. Memory 50 may include any suitable storage unit including, for example, a solid state non-volatile serial or parallel access memory. In certain embodiments, the memory may include a storage capacity of at least 32 MB. Suitable memory units include RAM, NVRAM, and Flash memory. It is also possible to use an internal microcontroller memory to store data, especially if microcontrollers are developed that include internal memory sizes greater than the currently available 64 kB sizes.

In the case that microcontroller 40 is configured to store raw data, microcontroller 40 may sample the outputs of the sensors onboard data collection unit 10 and simply store those values in memory 50. Those stored values can then later be downloaded from data collection unit 10 and processed using devices and/or systems external to data collection unit 10.

While it is possible to store raw data collected from the sensor devices, microcontroller 40 may also be configured to process the data sampled from the sensors of data collection unit 10 prior to storage in memory 50. For example, microcontroller 40 may be configured to calculate pulse rate, temperature, acceleration and average each calculated value over periods of up to thirty seconds, sixty seconds, or more to remove noise and enhance accuracy of the readings. Microcontroller 40 can be further configured to store these time averaged, filtered pulse rate/temperature/acceleration readings at preselected intervals (e.g., once or twice per minute). Such a scheme may conserve memory and/or power resources yet still provide useful information. These processed or conditioned data signals stored in memory, in certain cases, can even be more useful, as they may exhibit less noise and rapidly fluctuating values, which can detract from the reliability of the data.

Microcontroller 40 may be configured to condition the signals received from one or more of the sensors onboard data collection unit 10. During movement associated with physical activity, a significant amount of noise may be imparted to the signals generated by the onboard sensors. Such noise is especially prevalent in the data provided by the infrared sensors, which can be used to determine heart rate. Digital signal processing techniques may be employed to eliminate at least some of the noise from these signals and increase the accuracy of the heart rate calculation.

Microcontroller 40 may also be configured to determine when the user is at rest and when the user is exercising. In addition to using this information to control the data collection and storage rates, this information can be used, for example, in conjunction with a physical activity rewards allocation system to provide rewards-based incentives to the user of data collection unit 10. That is, the user of data collection unit 10 may receive rewards in the form of merchandise, merchandise discounts, currency, and/or free or discounted services based on the amount of time the user spends exercising and/or upon the level of physical exertion during exercise. The information may also be used to track physical activity levels for purposes of assessing the physical health of individuals. For example, the information may be tracked and used to determine the physical fitness, health, or well-being of private or public employees in order to provide worker incentives. Alternatively or additionally, this information could be used by the insurance industry to set rates/premiums tailored to an individual or discounted for a group of individuals participating in a physical activity tracking program.

Microcontroller 40 can be configured to determine when the user's level of activity qualifies as exercise. For example, microcontroller 40 can assimilate one or more of the user's pulse rate, temperature, and acceleration levels into a exercise evaluation score. Comparing the exercise evaluation score with a predetermined threshold level, microcontroller 40 can determine that the user is exercising when the exercise evaluation score exceeds the threshold.

The microcontroller's accuracy in determining the physical activity level or exertion level of a user can be refined according to any desired algorithm. In one embodiment, for example, microcontroller 40 may be configured to determine the relative reliability of the data provided by the sensors onboard data collection unit 10 and assign weighting factors (e.g., values between 0 and 1) to those outputs based on the perceived reliability of the data from each output. For example, if one of the infrared sensors is emitting a stable, oscillating output signal with a low noise level and another is emitting a noisy signal, then microcontroller 40 can assign a higher weighting factor to the higher quality signal and a lower weight to the noisy signal. In this way, microcontroller 40 can minimize the effects of extraneous noise and low quality data and maximize the measurement reliability when high quality data output signals are available.

Microcontroller 40 can be programmed with a common baseline threshold for use with all users of the disclosed data collection unit 10. Alternatively, microcontroller 40 may be used to calculate and periodically update a unique threshold determined for a specific user of a particular data collection unit. For example, as the user wears and uses data collection unit 10 over a period of time, microcontroller 40 may "learn" about the user by monitoring and storing quantities (e.g., heart rate, acceleration levels, and temperature) associated with periods during which the user is at rest and exercising. Using a predefined exercise threshold algorithm, the microcontroller can use this information to tailor the exercise threshold and store a new, updated exercise threshold based on the current fitness level of the user. The predefined algorithm may be loaded into the microcontroller's operating instruction set upon manufacture and may be updated via download from a central server system.

Ultimately, microcontroller 40 can be configured to determine when the user's level of physical activity surpasses the exercise threshold. Once the user exceeds the exercise threshold, the microcontroller may start a timer that monitors the amount of time the user spends above the exercise threshold. Further, via the sensed pulse rate, temperature, and acceleration levels measured, microcontroller 40 can determine and store a quantity that tracks the amount by which the user's physical activity exceeds the exercise threshold. This information, together or separate from exercise time, may be used by microcontroller 40 or, more preferably, a remote rewards allocation system to determine a rewards quantity accrued by the user during each period of exercise. Alternatively or additionally, this information can be used by a physical activity tracking system to determine worker incentives or to set/adjust insurance rates/premiums.

Data collection unit 10 may also include a feedback element, including, for example, a display, light, audible speaker, or other suitable sensory interface device. During periods when the user's physical activity exceeds the exercise threshold and qualifies for rewards accrual, microcontroller 40 may activate the feedback element to indicate to the user that the exercise threshold has been exceeded and rewards are being accrued. For example, an LED may be included that blinks during periods of qualifying exercise. In other embodiments, a speaker may emit an audible beep every few seconds during periods of qualifying exercise. In still other embodiments, a rewards indicator may be projected on a display during qualifying exercise sessions. Such an embodiment would be especially useful where data collection unit 10 was incorporated into a watch or other type of device including a display.

Microcontroller 40 of data collection unit 10 may be configured to control transmission of data to one or more remote locations. In one embodiment, microcontroller 40 can activate transceiver 26, as illustrated in FIG. 2, with a low duty cycle of less than about 1% to detect the presence of suitable data collection portals. A data collection portal 100, as shown in FIG. 2 can include any intended recipient of the data acquired by data collection unit 10. In one embodiment, a data collection portal 100 may be associated with a physical activity rewards allocation system and may forward the data received from data collection unit 10 to a central management facility that handles the operation of the rewards system. In another embodiment, the data collection portal 100 may be associated with a threshold exercise tracking system for purposes of determining the physical fitness, health, or well-being of private and public employees for worker incentives.

The data collection portal 100 may also be associated with an insurance rate/premium setting system that tailors rates or adjusts premiums based on the physical activity level of individuals and/or groups.

When data collection unit 10 detects a data collection portal 100 (e.g., either through a wired or wireless data connection) and communication is established, download of the data will commence, for example, after proper identification of the user and of the portal has been achieved. This may prevent eavesdropping by unauthorized parties. Identification of the user may include transmission of a unique code assigned to each data collection unit and/or user of the data collection unit. A user-selectable password can be used to allow data to be downloaded by the data collection portal. In other embodiments, passive identification of a user may displace the need for password protected downloads. For example, the microcontroller may be configured to determine and store a biological signature of an authorized user of the data collection unit. Such a signature may be determined using the same array of sensors used monitor temperature, pulse rate, and acceleration levels. Alternatively, one or more additional sensors (e.g., a skin pigment sensor, pH sensor, etc.) may be included to aid in user recognition.

One or more other devices, including, e.g., an RFID tag may be employed to facilitate the transmission of data to a data collection portal 100. For example, in response to a radio frequency interrogation signal, an RFID tag located on data collection unit 10 may power on using an onboard power source, such as battery 28, or using energy provided by the interrogation signal. The RFID tag can respond to the interrogation signal by transmitting data to a location/receiver remotely located with respect to data collection unit 10. The information transmitted may include information about data collection unit 10. For example, the transmitted information may include a signature code associated with a particular data collection unit 10. Additionally, the transmitted information may include any other data that may aid in recognition of the particular data collection unit 10.

One or more other devices, including, e.g., an RFID tag may be employed to facilitate the transmission of data to a data collection portal. For example, in response to a radio frequency interrogation signal, an RFID tag located on data collection unit 10 may power on using an onboard power source, such as battery 28, or using energy provided by the interrogation signal. The RFID tag can respond to the interrogation signal by transmitting data to a location/receiver remotely located with respect to data collection unit 10. The information transmitted may include information about data collection unit 10. For example, the transmitted information may include a signature code associated with a particular data collection unit 10. Additionally, the transmitted information may include any other data that may aid in recognition of the particular data collection unit 10.

Alternatively or additionally, an RFID tag or other similar device for transmitting data from data collection unit 10 (e.g., microcontroller 40 coupled with transceiver 26) may be used to transmit information about the user of data collection unit 10. This information can include, for example, medical emergency data, insurance information, name, home address, phone numbers, vital statistics, allergies, blood type, etc.

The transmitted information may also be used to recognize an individual wearer of data collection unit 10. For example, based on a particular piece of information (e.g., a signature code, name, address, etc.) an interrogating device or data portal may "recognize" the wearer of data collection unit 10. In response, the receiver of this information may take some action based on the recognition of the user of data collection unit 10. In certain embodiments, such information may be used to determine the location of a user of data collection unit 10; determine the frequency that the user visits a particular establishment, such as a health club, spa, pools; etc.

Data collection unit 10 may also be configured to detect potentially fraudulent use by a user. For example, because the user may receive rewards based on an indication by data collection unit 10 that the user had engaged in qualifying physical activity for a certain period of time, certain individuals may be motivated to simulate a state of physical activity, wear multiple data collection units, or engage in other types of fraudulent activity. With the robust sensor array included in data collection unit 10, the likelihood of data collection unit 10 being "fooled" by simulated physical activity is minimized.

Additionally, microcontroller 40 may be configured to generate and deliver a low power, low duty cycle pulse to metal contacts located, e.g., on the base of housing 20. These pulses may have a duration of less than about $100^{th}$ of a millisecond per pulse and will be transmitted over short distances around data collection unit 10. The same metal contacts on the base of housing 20 can also serve as an antenna and can aid in detection of similar signals in close proximity. When such a signal is detected, it may indicate that a user is wearing more than one data collection unit devices. If the detected signal remains constant over a certain period of time, further suggesting that more than one data collection unit 10 is in use by a single user, then either the emitting or detecting data collection unit, or both, may be configured to shut down.

Suitable data collection portals 100 may include those located within a predetermined distance from data collection unit 10. In certain embodiments, data collection unit 10 may be configured to transmit data to portals 100 located within about ten feet. In other embodiments, this transmission distance may be extended up to about 50 feet.

Once transmission of data stored in data collection unit 10 commences, a handshaking process may be employed to validate the integrity of the data transmitted and to request retransmission of the data, if necessary. After data collection unit 10 establishes that the data has been successfully transmitted to the data collection portal 100, microcontroller 40 can delete the previously stored data.

Transmission of data to a data collection portal 100 may also be controlled based on the availability of stored data. For example, if no new data has been stored in memory 50 since the last successful download, then microcontroller 40 may determine that there is nothing to transmit. Under these conditions, microcontroller 40 may forego searching for a suitable data collection portal 100 within range and will leave the data collection unit transceiver 26 powered down until data is subsequently stored in memory.

Other schemes for data transmission initiation may be employed. For example, rather than the microcontroller periodically searching for a suitable data collection portal 100 within range, microcontroller 40 may be configured to simply respond to an interrogation signal continuously or periodically emitted from a data collection portal 100. If microcontroller 40 receives such an interrogation and determines that the emitting data collection portal 100 is within transmission range, then microcontroller 40 can activate transceiver 26 and commence data transmission.

Data transmission may be accomplished via any suitable scheme for transmission of data. In one embodiment, the data stored in the data collection unit may be transferred via a wired connection including a cable and cable interface. In one embodiment, data transmission can be accomplished via a USB data cable that enables charging of data collection unit 10 while data is downloaded. Data transmission may also be accomplished via a wireless connection including a radio frequency or optical transmission link. In certain embodiments, for example, data collection unit 10 can be Bluetooth or Zigbee enabled or may transmit data via an infrared optical link.

In certain embodiments, data transmission can extend beyond the limits of the onboard transceiver. For example, using a Bluetooth enabled data collection unit coupled with an external device, such as a cell phone, PDA, personal computer, etc., data can be relayed from data collection unit 10 through the external device and on to a data collection portal or even directly to the management facility.

Data collection unit 10 may include any suitable power source for meeting the power requirements of the unit. For example, data collection unit 10 may include a replaceable or rechargeable battery 28. In certain embodiments, three-volt lithium batteries contained within a 1.2 cm package may be included in data collection unit 10. Additionally, or alternatively, a solar cell may be included either alone or in combination with one or more batteries. In addition to serving as a stand alone power source, the solar cell may also function to recharge the batteries. In another embodiment, a motion activated regeneration device may be included for purposes of powering the data collection unit and/or recharging batteries.

It will be apparent to those skilled in the art that various modifications and variations can be made in the disclosed sensor unit without departing from the scope of the disclosure. Other embodiments of the disclosed systems and methods will be apparent to those skilled in the art from consideration of the specification and practice of the disclosure disclosed herein.

What is claimed is:

1. A physical activity data collection unit, including:
   two or more infrared sensors arranged on the data collection unit such that when the data collection unit is worn by a user, the two or more infrared sensors are positioned adjacent to a wrist of the user, the two or more infrared sensors being configured to provide an output indicative of a pulse rate of the user of the physical activity data collection unit;
   at least one temperature sensor configured to provide an output indicative of at least a body temperature of the user;
   at least one accelerometer configured to provide an output indicative of movements of the user; and
   a microcontroller configured to:
      receive, from the two or more infrared sensors, two or more output signals, including one output signal received from each one of the two or more infrared sensors;
      determine a noise level value for each one of the two or more received output signals;
      determine a weighting factor for each one of the two or more received output signals based on the noise level value determined for each one of the two or more received output signals, wherein a first weighting factor determined for an output of one of the two or more infrared sensors having a first noise level is greater than a second weighting factor determined for an output of another of the two or more infrared sensors having a second noise level higher than the first noise level;
      obtain weighted outputs by assigning the determined weighting factors to corresponding ones of the two or more received output signals;

determine a pulse rate, a body temperature, and movement characteristics of the user of the data collection unit based on the weighted outputs, the output provided by the at least one temperature sensor, and the output provided by the at least one accelerometer, respectively;

determine a physical exertion level of the user based on one or more of the pulse rate, the body temperature, or the movement characteristics of the user; and store, in a memory, data indicative of the physical exertion level during a time period during which the physical exertion level exceeds a predetermined threshold.

2. The physical activity data collection unit of claim 1, further including a transceiver, and wherein the microcontroller is further configured to transmit data indicative of the exertion level of the user to an external data collection portal.

3. The physical activity data collection unit of claim 2, wherein the microcontroller is configured to determine the presence of stored physical exertion data and automatically initiate transmission of the stored data upon determining that the data collection unit has come within a predetermined range of the data collection portal.

4. The physical activity data collection unit of claim 2, wherein the microcontroller is configured to determine the presence of stored physical exertion data and initiate transmission of the stored data upon receiving an interrogation signal from the data collection portal.

5. The physical activity data collection unit of claim 2, wherein the transceiver is configured to transmit data via an optical or radio frequency link.

6. The physical activity data collection unit of claim 1, wherein the microcontroller is further configured to update the predetermined threshold based on a current fitness level of the user.

7. The physical activity data collection unit of claim 1, wherein the at least one temperature sensor includes at least one of a thermocouple, diode, resistive temperature device, or infrared device.

8. The physical activity data collection unit of claim 1, wherein the two or more infrared sensors each include an infrared transceiver unit.

9. The physical activity data collection unit of claim 8, wherein the pulse rate is determined by monitoring changes in the blood oxygen saturation level.

10. The physical activity data collection unit of claim 1, wherein the microcontroller is configured to condition output signals provided by the two or more infrared sensors, the at least one temperature sensor, or the at least one accelerometer and store the conditioned signals in the memory.

11. The physical activity data collection unit of claim 1, wherein the microcontroller is configured to recognize potentially fraudulent use of the data collection unit and take at least one action in response to the recognized potentially fraudulent use.

12. The physical activity data collection unit of claim 11, wherein the microcontroller is configured to:
generate a signal to be emitted by the data collection unit;
detect the presence of similar signals generated in the vicinity of the data collection unit; and
shut down the data collection unit if potentially fraudulent use is recognized based on the detection of the similar signals.

13. The physical activity data collection unit of claim 1, further including an RFID tag to aid in recognition of the data collection unit or the user of the data collection unit.

14. The physical activity data collection unit of claim 1, wherein the microcontroller is configured to communicate a unique code associated with the data collection unit to aid in recognition of the data collection unit.

15. The physical activity data collection unit of claim 1, wherein the microcontroller is configured to apply variable weights to the outputs of the at least one temperature sensor or the at least one accelerometer when determining the physical exertion level of the user.

16. A physical activity data collection unit, including:
one or more infrared sensors configured to provide an output indicative of a pulse rate of a user of the physical activity data collection unit;
at least one temperature sensor configured to provide an output indicative of at least a body temperature of the user;
at least one accelerometer configured to provide an output indicative of movements of the user; and
a microcontroller configured to:
determine and store a first pulse rate for the user during a time period when the user is at rest;
determine and store a second pulse rate for the user during a time period when the user is exercising;
calculate a unique exercise threshold specific to the user based on the first pulse rate for the user determined during a time period when the user is at rest and based on the second pulse rate for the user determined during a time period when the user is exercising;
sample the outputs of the one or more infrared sensors, the at least one temperature sensor, and the at least one accelerometer;
determine an exercise evaluation score for the user based on the sampled outputs; and
store, in a memory, data derived from the sampled outputs of the one or more infrared sensors, the at least one temperature sensor, and the at least one accelerometer based on whether the exercise evaluation score exceeds the calculated exercise threshold specific to the user.

17. The physical activity data collection unit of claim 16, further including a transceiver, and wherein the microcontroller is further configured to transmit data stored in the memory to an external data collection portal.

18. The physical activity data collection unit of claim 16, wherein the microcontroller is configured to condition the data prior to storing the data in the memory.

19. The physical activity data collection unit of claim 16, wherein the microcontroller is configured to recognize potentially fraudulent use of the data collection unit and take at least one action in response to the recognized potentially fraudulent use.

20. The physical activity data collection unit of claim 19, wherein the microcontroller is configured to:
generate a signal to be emitted by the data collection unit;
detect the presence of similar signals generated in the vicinity of the data collection unit; and
shut down the data collection unit if potentially fraudulent use is recognized based on the detection of the similar signals.

21. The physical activity data collection unit of claim 16, further including an RFID tag to aid in recognition of the data collection unit or the user of the data collection unit.

22. The physical activity data collection unit of claim 16, wherein the microcontroller is configured to communicate a unique code associated with the data collection unit to aid in recognition of the data collection unit.

23. A physical activity data collection unit, including:
a pulse rate sensor including an infrared transmitter receiver arranged on the data collection unit such that when the data collection unit is worn by a user, the infrared transmitter receiver is positioned adjacent to a wrist of the user;

a body temperature sensor; and a microcontroller configured to
- determine a pulse rate of the user based on an output from the pulse rate sensor;
- determine a body temperature of the user based on an output from the body temperature sensor;
- determine a physical exertion level of the user based on one or more of the pulse rate and body temperature of the user; and
- when the physical exertion level of the user exceeds a predetermined exercise threshold, start a timer that monitors the amount of time the user spends above the exercise threshold and store in memory a quantity that tracks an amount by which the user's physical exertion level exceeds the predetermined exercise threshold.

24. The physical activity data collection unit of claim 23, further including a transceiver, and wherein the microcontroller is further configured to transmit data indicative of the exertion level of the user to an external data collection portal.

25. The physical activity data collection unit of claim 23, wherein the microcontroller is further configured to update the predetermined exercise threshold based on a current fitness level of the user.

* * * * *